United States Patent [19]
Toda

[11] Patent Number: 4,894,495
[45] Date of Patent: Jan. 16, 1990

[54] WATERTIGHT ELECTRICAL CONTACT UNITS

[76] Inventor: Masato Toda, Hachioji, Japan

[21] Appl. No.: 222,339

[22] Filed: Jul. 18, 1988

Related U.S. Application Data

[63] Continuation of Ser. No. 19,352, Feb. 26, 1987, abandoned.

[30] Foreign Application Priority Data

Mar. 13, 1986 [JP] Japan ................................. 61-055854

[51] Int. Cl.⁴ ............................................ H01R 33/96
[52] U.S. Cl. ................................ 200/51.12; 200/302.1
[58] Field of Search ......................... 200/302.1–302.3, 200/159 B, 51.12; 128/4–6, 204.23, 303.15; 439/736, 819, 824, 246, 247, 248; 277/212 C

[56] References Cited

U.S. PATENT DOCUMENTS

| | | | |
|---|---|---|---|
| 1,405,537 | 2/1922 | Milton | 200/159 B |
| 1,530,345 | 3/1925 | Benson | 200/51.12 |
| 2,925,479 | 2/1960 | Marasco | 200/302.1 |
| 3,879,586 | 4/1975 | Durocher et al. | 200/159 B |
| 4,356,344 | 10/1982 | Carey | 439/736 |

FOREIGN PATENT DOCUMENTS

| | | | |
|---|---|---|---|
| 682123 | 5/1930 | France | 200/159 B |
| 940493 | 5/1964 | France | 200/159 B |
| 54-28291 | of 1979 | Japan . | |

Primary Examiner—Linda J. Sholl

[57] ABSTRACT

A watertight electrical contact unit is integrally molded by embedding a contact member in a watertight elastic member which is watertightly secured to a body for mounting the contact unit.

11 Claims, 4 Drawing Sheets

WATERTIGHT ELECTRICAL CONTACT UNITS

This is a continuation of application Ser. No. 19,352 filed on February 26, 1987, now abandoned.

BACKGROUND OF THE INVENTION

The present invention relates to a watertight electrical contact unit, and more particularly, to a watertight electrical contact unit comprising a contact member integrally molded with a watertight elastic member.

Recently, there has been a growing demand to an endoscope for sterilization and a great deal of effort has been made on the perfect water-tightness. An electric contact unit provided on a watertight endoscope is generally fixed to the endoscope with a bonding agent so as to make it watertight. A camera to be connected to such a watertight endoscope requires the water-tightness. However, it raises a problem of making an electrical contact unit watertight. To solve this, as shown in Japanese Laid Open Utility Model Publication Sho 54/1979-28291, a watertight cover which has been devised for an early electrical contact unit of an endoscope is generally employed.

With such a conventional watertight cover, however, it is required to mount it on an electrical contact unit during a sterilization process, thus it being time-consuming. In addition, with a watertight cover mounted, the inside of the cover will not be sterilized with dirty portions remained.

Furthermore, an electrical contact unit for a camera to be connected to an endoscope having an adhesively fixed electrical contact unit should be movable with respect to the fixed electrical contact unit. To this end, it is conceivable that the water-tightness of a movable portion is generally achieved by employing an O ring or the like. In this case, however, the connection of an electrical contact unit increases in size and water stays on an O ring area, resulting in poor draining, propagation of various germs, adherence of a disinfectant and the like.

SUMMARY OF THE INVENTION

It is an object of the present invention to provide a watertight electrical contact which is compact, simple in structure and reliable in water-tightness.

According to the present invention, an electrical contact unit has a contact member whose middle portion is integrally molded with an elastic member of water-tightness, the elastic member being watertightly secured to an apparatus body so as to make the electrical contact unit watertight and to allow the unit to be in the contact condition with a contact pressure by the elastic force of the elastic member.

Further, according to the present invention, a contact member is integrally molded with an elastic member of water-tightness and has no sliding part, so that an electrical contact unit is made watertight with a compact and simple structure. Thus, the electrical contact unit is impervious to water and medical fluid and is able to prevent adherence of water and medical fluid. In addition, the electrical contact unit has the outer surface of reduced ruggedness, so that water is easily wiped and drained.

DETAILED DESCRIPTION OF PREFERRED EMBODIMENTS

Figure 1:
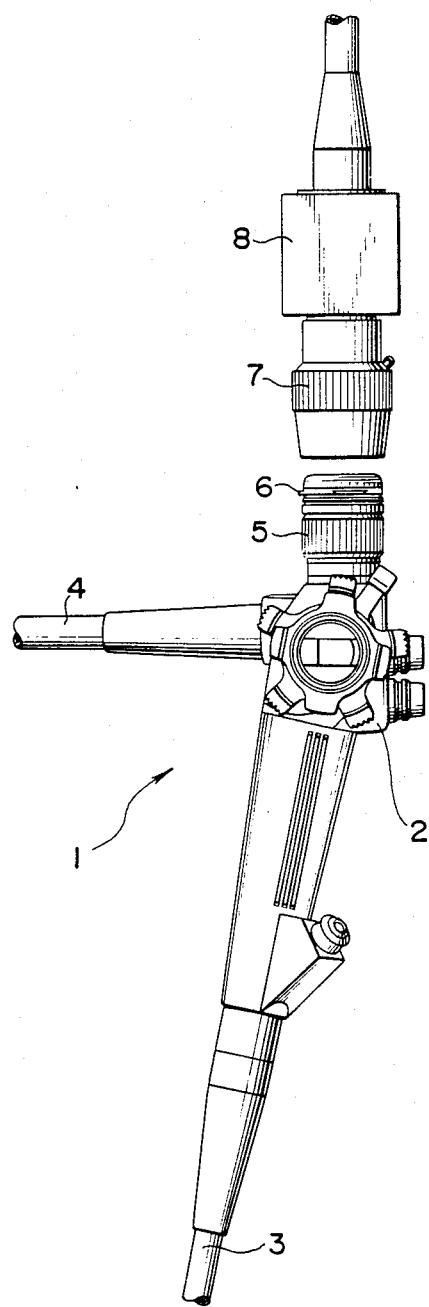
FIG. 1 is a side view showing correlation between an adapter having an electrical contact unit of the present invention and an endoscope.

In FIG. 1, an endoscope 1 comprises an operation portion 2, an insertion portion 3 extended from the operation portion 2, a universal cord 4 in which a light guide and the like are housed, and an eyepiece 5 provided on the opposite side of the insertion portion 3. The eyepiece 5 has a mount 6 at the outer periphery thereof to which an external camera, various adapters and the like are connected. An adapter 7 has a front mount provided at the front end thereof to which the mount 6 of the endoscope 1 is connected and a rear mount provided at the rear end thereof in which a television camera 8 or the like is connected to the eyepiece 5 of the endoscope 1. The adapter 7 includes a view finder (not shown) which projects from the side plane of the adapter 7 and which splits and guides light beams within the adapter 7.

Figure 2:
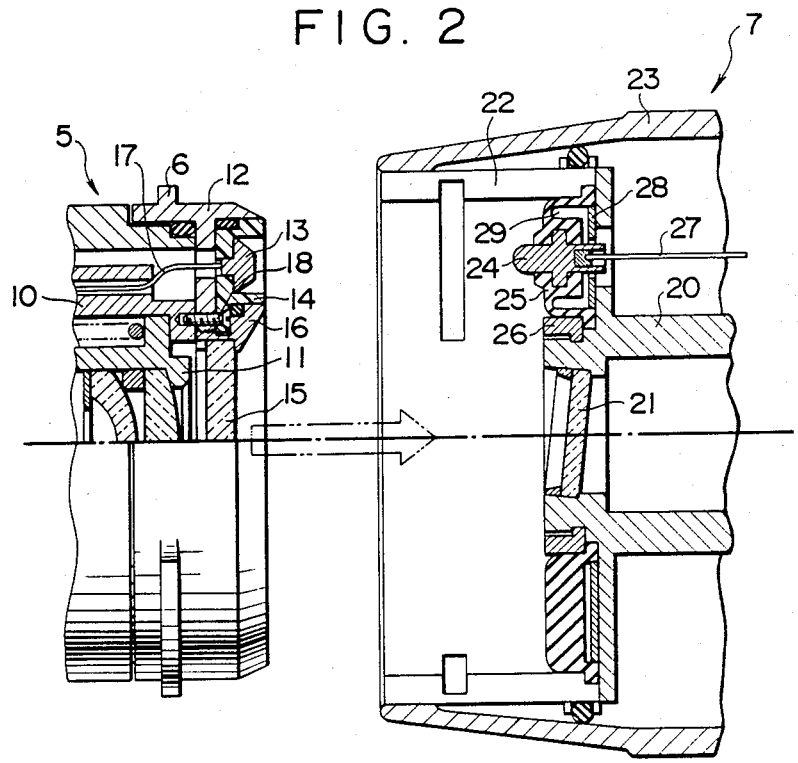
FIG. 2 is a sectional view of essential parts of a first embodiment of a watertight electrical contact unit according to the present invention.

FIG. 2 is a sectional view of essential parts of the eyepiece 5 in the endoscope 1 and the adapter 7. The eyepiece 5 has an eyepiece barrel 10 fixed to a base (not shown). An eyepiece lens 11 is mounted within the inside of the barrel 10 such that the lens 11 is slidable in its axial direction. A mount member 12 in which the mount 6 is formed on the outer periphery thereof and a frame 14 which holds an electrical contact member 13 are secured to the barrel 10 by means of a screw 18. In addition, a holding frame 16 of a cover glass 15 is threadedly secured to the mount member 12. These interconnections are made watertight by providing with O rings or the like. The electrical contact member 13 of the eyepiece 5 is adhesively fixed to the frame 14. A conductor 17 is soldered within the electrical contact member 13.

The adapter 7 has a tubular body 20 within which a beam splitter and the like (not shown) which splits light beams to an adapter lens and the view finder are housed. A cover glass 21 is watertightly fixed to the end of the tubular body 20. A mount member 22 in the adapter 7 is mounted on the periphery of the body 20. An adapter outer wall 23 is mounted on the outside of the mount member 22 with a means (not shown). In addition, an electrical contact member 24 in the adapter 7 which is to be in contact with the above stated contact member 13 is integrally molded with a watertight elastic member 25 which is formed of rubber in a doughnut shape such that part of the contact member is embedded into the elastic member. The elastic member 25 has its outer peripheral edge urgingly held in the mount member 22 and its inner peripheral edge urgingly held in the tubular body 20 with a holding ring 26. A conductor 27 is soldered within the contact member 24. A plate 28 for preventing sideways transformation of the elastic member is inserted between the tubular body 20 and the elastic member 25 which plate has an opening through which the contact member 24 passes.

The elastic member 25 is formed of a high disinfectant-resisting material such as silicone rubber. The elastic member 25 has its outer surface having an area to be in contact with another contact member and its inner surface through which a soldering portion of the conductor 27 projects and into which a flanged portion of the contact member 24 is embedded. In addition, a groove 29 is provided in the elastic member 25 around the contact member 24 so as to allow the contact member 24 to easily move in the axial direction thereof.

When the adapter 7 is mounted on the eyepiece 5 of the endoscope 1 through the mount members 12, 22, the electrical contact member 24 is brought into contact with the contact member 13 with a contact pressure by the elastic force of the elastic member 25. In addition, since the electrical contact member 24 is integrally formed with the watertight elastic member 25, the contact member 24 and the elastic member 25 are placed in close contact with each other, so that the tubular body 20 is maintained in water-tightness. The plate 28 prevents the soldering portion of the contact member 24 from falling sideways when the contact member 24 is inclined and also prevents the elastic member 25 from protruding inwardly when the elastic member 25 is secured in place.

Figure 3:
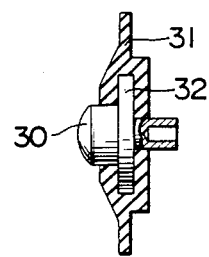
FIG. 3 is a sectional view of essential parts of a second embodiment of a watertight electrical contact unit according to the present invention.

FIG. 3, a second embodiment of the present invention, shows only an electrical contact member having an elastic member. In the second embodiment, in which there is a sufficient space in an electrical contact unit for making an electrical contact member large, an electrical contact member 30 which is flat and has a flanged portion 32 of a large diameter is integrally molded with a watertight elastic member 31. The elastic member 31 is in the form of a radially flat thin board, unlike the first embodiment, without providing a groove around the contact member 30. With the second embodiment, it is possible to prevent the contact member 30 from falling sideways during connection since the contact member 30 is flat.

Figure 4:
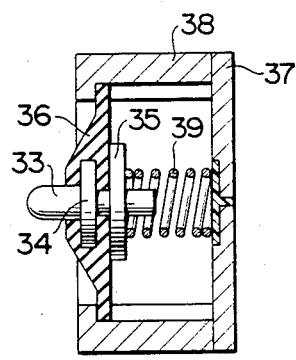
FIG. 4 is a sectional view of essential parts of a third embodiment of watertight electrical contact unit according to the present invention.

FIG. 4 shows a third embodiment of the present invention, where the contact pressure of an electrical contact member is desirous to be higher than the elastic pressure of a watertight elastic member. An electrical contact member 33 has first and second flanges 34, 35. Only the first flange 34 is molded within a watertight elastic member 36. The electrical contact member 33 has its peripheral edge secured through the elastic member 36 to the holding frame 38 which is provided on a unit body 37. A coiled spring 39 is interposed between the body 37 and the second flange 35 in an electrically insulated manner. A leaf spring or the like may be substituted for the coiled spring 39.

Figure 5:
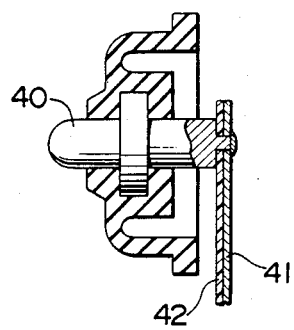
FIG. 5 is a sectional view of essential parts of a watertight electrical contact unit according to the present invention where a flexible base plate is connected thereto.

FIG. 5 shows a watertight electrical contact member according to the present invention where a flexible base plate 42 on which a pattern 41 is formed is connected to an electrical contact member 40 in place of the conductor 27 soldered to the electrical contact member 24 shown in FIG. 2. The number of the electrical contact members to be connected to a single flexible base plate may be one or more.

In the foregoing, while electrical contact units for use in endoscopes are described, these can be used for various purposes, not limited to endoscopes and for obtaining a contact pressure while in use without using a coiled spring, leaf spring or the like. In addition, the contact pressure can be optionally changed by selecting thickness, hardness and material of the elastic member in which the electrical contact member is embedded.

The number of the electrical contact members may be one or more in the contact unit. The electrical contact unit of the present invention may be applied to both of a pair of electrical contact units.

What is claimed is:

1. Apparatus comprising:
    component mounting means including first and second mounting sections relatively movable between first and second positions;
    electrical switch means including first and second cooperating contact members that are carried by the respective first and second mounting sections, said cooperating contact members being engaged when said mounting sections are in said first position and are disengaged when said mounting sections are in said second position;
    a watertight electrical contact unit secured to said first mounting section, said contact unit including a watertight elastic member and said first contact member;
    said first contact member including:
    (a) a contact portion at a first side of said elastic member;
    (b) a conductor connecting portion for electrically connecting said first contact member to a conductor when said first and second mounting sections are in said first position and for connecting said first contact member to the conductor when said first and second mounting sections are in said second position, said conductor connecting portion being located at a side of said elastic member which is opposite to said first side of said elastic member; and
    (c) another portion excluding said contact portion and said conductor connecting portion;
    with said mounting sections in said first position said contact portion being in direct engagement with said second contact member;
    said elastic member being interposed between said first mounting section and said first contact member, and being a molded unitary body wherein said another portion of said contact member is embedded;
    said contact portion being operatively positioned to engage said second contact when the latter is disposed forward of said contact portion;
    said elastic member including an annular groove open at its rear facing side and formed around said first contact member so as to facilitate movement of said first contact member in the axial direction relative to said first mounting section when said first contact member is being placed in contact with said second contact member.

2. Apparatus according to claim 1, in which said contact member has a flanged portion at the middle portion thereof, said flanged portion being embedded in said elastic member, said another portion including said flanged portion.

3. Apparatus according to claim 1 further including a plate member for preventing said conductor connecting portion from falling sideways; said plate member being interposied between said elastic member and said first mounting section; said plate member extending around the conductor connecting portion.

4. Apparatus according to claim 1, in which said elastic member has its peripheral edge formed as a fixing portion to said first mounting section.

5. Apparatus according to claim 1, in which said elastic member is formed of material of high desinfectant resistance such as silicone rubber.

6. Apparatus according to claim 1, in which said first contact member has first and second flanged portions, only said first flanged portion being molded by being embedded in said elastic member, and a spring being interposed between said second flanged portion and said first mounting section.

7. Apparatus comprising:
component mounting means including first and second mounting sections relatively movable between first and second positions;
electrical switch means including first and second cooperating contact members that are carried by the respective first and second mounting sections, said cooperating contact members being engaged when said mounting sections are in said first position and are disengaged when said mounting sections are in said second position;
a watertight electrical contact unit secured to said first mounting section, said contact unit including a watertight elastic member and said first contact member;
said first contact member including:
  (a) a contact portion at a first side of said elastic member;
  (b) a conductor connecting portion for electrically connecting said first contact member to a conductor when said first and second mounting sections are in said first position and for connecting said first contact member to the conductor when said first and second mounting sections are in said second position, said conductor connecting portion being located at a side of said elastic member which is opposite to said first side of said elastic member; and
  (c) another portion excluding said contact portion and said conductor connecting portion;
with said mounting sections in said first position said contact portion being in direct engagement with said second contact member;
said elastic member being interposed between said first mounting section and said first contact member, and being a molded unitary body wherein said another portion of said contact member is embedded;
said contact portion being operatively positioned to engage said second contact when the latter is disposed forward of said contact portion, and when so engaged said elastic member is deflected rearward thereby establishing a forwardly directed biasing force that contributes at least partially to established butt contact pressure between said contact portion and said second contact engaged thereby.

8. Apparatus according to claim 7 also including a spring disposed behind said elastic member and operatively engaged with said first contact member to contribute to said contact pressure when said elastic member is deflected rearward.

9. Apparatus according to claim 8, in which said elastic member includes an annular groove having a depth that is substantially greater than its width, said groove being open at its rear facing side and formed around said first contact member so as to facilitate movement of said first contact member in the axial direction relative to said first mounting section when said first contact member is being placed in contact with said second contact member.

10. Apparatus according to claim 7, in which said first contact member and elastic member are both integrally molded in an axially flat thin board form.

11. Apparatus according to claim 7, in which said first contact member has a flexible base plate on which a pattern is formed connected thereto.

* * * * *